United States Patent [19]
Bockstahler

[11] 3,994,976
[45] Nov. 30, 1976

[54] SUBSTITUTED PHENYLTHIOAMIDINES

[75] Inventor: Earl R. Bockstahler, Indianapolis, Ind.

[73] Assignee: The Dow Chemical Company, Midland, Mich.

[22] Filed: Aug. 11, 1975

[21] Appl. No.: 603,832

Related U.S. Application Data

[62] Division of Ser. No. 486,705, July 8, 1974, Pat. No. 3,933,912, which is a division of Ser. No. 401,474, Sept. 27, 1973, Pat. No. 3,847,986, which is a division of Ser. No. 257,940, May 30, 1972, Pat. No. 3,775,478.

[52] U.S. Cl. .......................... 260/564 R; 260/501.14
[51] Int. Cl.² ........................................ C07C 123/00
[58] Field of Search ................... 260/564 R, 501.14

[56] References Cited
UNITED STATES PATENTS 3,790,679  2/1974  Shea ............................... 260/564 R

OTHER PUBLICATIONS

Craver et al., J. Pharmacology & Experimental Therapeutics, vol. 99, pp. 353–361, (1950).

*Primary Examiner*—Gerald A. Schwartz
*Attorney, Agent, or Firm*—C. Kenneth Bjork

[57] ABSTRACT

Substituted phenylthioamidine compounds such as 2-(4-chlorophenylthio)acetamidine; 2-(4-chlorophenylthio)-acetamidoxime; and their pharmaceutically-acceptable salts are prepared by the reaction of a substituted phenylthioacetonitrile with hydroxylamine hydrochloride or with methanol followed by ammonium chloride. The compounds have antimicrobial activity and also inhibit ADP-induced aggregation of blood platelets.

2 Claims, No Drawings

SUBSTITUTED PHENYLTHIOAMIDINES

CROSS-REFERENCE TO RELATED APPLICATION

This is a division, of application Ser. No. 486,705 Filed July 8, 1974, now U.S. Pat. No. 3,933,912, which is a division of Ser. No. 401,474, filed Sept. 27, 1973 now U.S. Pat. No. 3,847,986 which in turn is a division of Ser. No. 257,940, filed May 30, 1972 now U.S. Pat. No. 3,775,478

BACKGROUND OF THE INVENTION

1. Description of the Prior Art

The substituted phenylthioamidine compounds of the invention can be prepared by procedures analogous to known methods. Typical methods which can be employed include the reaction of an arylthioacetonitrile with hydroxylamine hydrochloride in the procedure similar to that of Bruderlein, U.S. Pat. No. 3,334,137, or the reaction of a phenylthioacetonitrile with methanol in the presence of sodium methylate, followed by reaction with ammonium chloride, in a procedure analogous to that of Schaefer and Peters, J. Org. Chem. 26, 412 (1961).

2. Summary of the Invention

This invention is directed to substituted arylthioamidine compounds and is particularly directed to substituted phenylthioacetamidine compounds and their pharmaceutically-acceptable salts, the compounds corresponding to the formula:

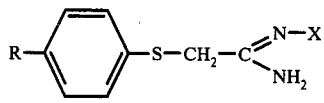

wherein R represents tertiary butyl (tert-butyl) or halo and X represents hydrogen or hydroxyl. The compounds of the invention are solids or viscous liquids at ordinary temperatures, and are variously soluble in conventional solvents such as water, alcohols, ether, benzene, chlorinated hydrocarbons and the like. The free base compounds are generally less soluble in water than the salts, particularly under alkaline conditions, while the pharmaceutically-acceptable salts are generally of moderate to good solubility in water and alcohols.

In the present specification, the term halo is employed to designate one of the halogen moieties, fluoro, chloro, bromo or iodo. The compounds of the invention wherein X is hydroxyl are named as acetamidoximes. For convenience, both the acetamidines and corresponding oximes can be referred to generically as substituted amidines. The term pharmaceutically-acceptable salt as herein employed refers to salts of a substituted amidine which are substantially non-toxic at dosages consistent with good pharmacological activity. Such pharmaceutically-acceptable salts include non-toxic acid addition salts with inorganic acids such as hydrochloric, hydrobromic, sulfuric or phosphoric acid, or with organic acids such as acetic, succinic, malic, maleic, tartaric or citric acid, or with organic sulfonic acids such as methane-sulfonic or p-toluene-sulfonic acid.

The substituted amidines of the invention have been found to be useful for administration to laboratory animals in the study of drug effects on the cardiovascular system, and have been found to be particularly useful in inhibiting aggregation of blood platelets. The compounds wherein R is halo are highly active against bacterial organisms commonly involved in infections of the urinary tract, and can be administered orally to animals to impart antimicrobial activity to the urine in combatting microorganisms such as Ps. aeruginosa, E. coli and Proteus vulgaris, organisms commonly involved in urinary tract infections.

The substituted amidines of the invention are prepared by the reaction of the corresponding substituted phenylthioacetonitrile with hydroxylamine in aqueous alcohol (to prepare the acetamidoximes), or with methanol in the presence of sodium methylate to prepare the corresponding imidate followed by reaction of the imidate intermediate with aqueous ammonium carbonate.

In preparing the acetamidoximes, the reaction proceeds when the substituted phenylthioacetonitrile and hydroxylamine are contacted and mixed in the presence of a base such as sodium carbonate, and an inert liquid reaction medium such as aqueous ethanol. The reaction proceeds at temperatures from about 50° C. to about 75° C. and is preferably carried out at temperatures of from about 65° to about 70° C. The exact proportions of the reactants to be employed can be varied, however, the reaction consumes the reactants in equimolar proportions and the use of the reactants in such proportions, or with a slight excess of the hydroxylamine reactant, is preferred. Greater than two fold molar excesses of hydroxylamine is neither necessary nor desirable. The reaction is generally complete in about six to twelve hours, depending on the temperature employed. The product can be separated by evaporation of the reaction medium under reduced pressure, taking up the residue in water and aqueous acid to neutralize remaining base, washing with organic solvents, and adding base to make the mixture alkaline. The amidoxime separates as a solid or an oil which solidifies on treatment by conventional techniques such as cooling, trituration, scratching, etc. The solid product can be purified by recrystallization from water alcohols or the like. Alternatively, the product can be converted to a pharmaceutically-acceptable salt and purified as the salt.

The acetamidines of the invention are conveniently prepared by a two-step process illustrated below:

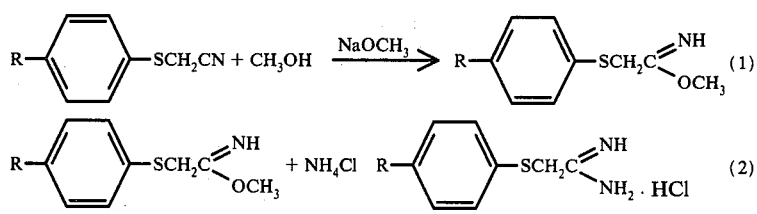

in the above formulae, the moiety R has the significance first set out above.

The first step proceeds when the substituted phenylthioacetonitrile is intimately mixed with methanol and a catalytic amount of sodium methylate. The reaction proceeds at temperatures of from about 0° C. to 70° C., and is conveniently carried out at room temperature. After the reaction mixture has been held for a period sufficient for the production of sufficient amount of the imidate intermediate (generally from about 3 to about 12 hours), an ammonium salt is added to the mixture and the mixture is maintained at a temperature within the same reaction temperature range until the second step is substantially complete, generally about 12 to 24 hours at room temperature. The product can be separated by evaporation of the reaction medium, and is obtained as the salt with the anion furnished by the ammonium salt reactant. Ammonium chloride is a preferred ammonium salt reactant, although ammonium salts with other pharmaceutically-acceptable anions can also be employed to produce other salts, such as the hydrobromide, sulfate, carbonate, etc. The product can be purified by conventional techniques such as washing and recrystallization from water, alcohols, dioxane and alcohols, and the like. Alternatively, it can be converted to the free base.

The pharmaceutically-acceptable salts of the free base substituted amidines can be prepared by dissolving the free base in a minimal amount of alcohol or ether and adding an alcohol solution of an acid such as hydrochloric acid, hydrobromic acid, malic acid, maleic acid or succinic acid until precipitation of the corresponding salt is complete. The salt can further be purified by recrystallization or converted to the free base form.

The free base substituted amidine can be prepared by hydrolysis of the salt in aqueous base. The salt is mixed with a molar equivalent amount of sodium hydroxide in aqueous solution, excess aqueous sodium carbonate or the like, after which the free base can be separated by extraction with an organic solvent. The solvent can be removed by conventional methods such as evaporation or distillation. The product can be purified by conventional procedures such as washing or recrystallization.

DESCRIPTION OF THE PREFERRED EMBODIMENTS

The following examples illustrate the invention but are not to be construed as limiting the same.

EXAMPLE 1

10.6 Grams (0.1 mole) of sodium carbonate is dissolved in 40 milliliters of water and 16.7 grams (0.24 mole) of hydroxylamine hydrochloride are added. The mixture is then added to a solution of 36.7 grams of 4-chlorophenylthioacetonitrile in 350 milliliters of aqueous 95 percent ethanol. The resulting mixture is heated with stirring for about 5 hours at a temperature of 65°–70° C., then evaporated to dryness under reduced pressure. The residue is taken up in water and hydrochloric acid is added to make the aqueous mixture slightly acid to litmus. The mixute is filtered, and the filtrate is concentrated by evaporation under reduced pressure, whereupon the 2-(4-chlorophenylthio)acetamidoxime hydrochloride product crystallizes. The product is separated by filtration, and the 2-(4-chlorophenylthio)acetamidoxime hydrochloride product is purified by recrystallization twice from a mixture of methanol and dioxane, and once from water, and found to melt at a temperature of 153°–155° C. The product is found by elemental analysis to have carbon and hydrogen contents of 38.2 and 4.3 percent, respectively, as compared to the theoretical contents of 38.0 and 4.0 percent, respectively, calculated for the named structure.

In a similar procedure, the following acetamidoximes can be prepared: 2-(4-bromophenylthio)acetamidoxime, melting at 82°–85° C.; 2-(4-fluorophenylthio)acetamidoxime hydrochloride (molecular weight 236); 2-(4-iodophenylthio)acetamidoxime hydrochloride (molecular weight 345); and 2-(4-tert-butylphenylthio)acetamidoxime hydrochloride, melting at 138°–140° C.

EXAMPLE 2

0.23 Gram (0.01 mole) of sodium is dispersed carefully in 50 milliliters absolute methanol to prepare a mixture of sodium methylate in methanol. 0.1 Mole (18.4 grams) of 2-(4-chlorophenylthio)acetonitrile is added to the mixture and the resulting mixture is stirred at room temperature for about four hours. The methyl 2-(4-chlorophenylthio)acetamidate intermediate thus produced is not separated. 5.9 Grams (0.11 mole) of ammonium chloride is added directly to the mixture, and stirring at room temperature is continued for about 18 hours. The mixture is evaporated under reduced pressure, and the residue is purified by recrystallization from water and then from ethanol, and dried. The 2-(4-chlorophenylthio)acetamidine hydrochloride product is found to melt at a temperature of 194°–196° C. By elemental analysis, the product is found to have carbon and hydrogen contents of 40.4 and 4.5 percent, respectively, as compared to the contents of 40.5 and 4.3 percent, respectively, calculated for the named structure.

In a substantially similar procedure, 2-(4-tert-butylphenylthio)acetamidine hydrochloride, melting at 181°–¾° C.; 2-(4-bromophenylthio)acetamidine hydrochloride, melting at 186°–188° C., and the corresponding 4-fluoro and 4-iodo compounds are prepared.

In employing the substituted amidine compounds of the invention in the control of microorganisms such as bacteria, protozoa and fungi, an antimicrobial amount of one or more of the compounds is applied to the organisms, their habitats or to substrates subject to microbial attack. The compounds can be applied by conventional procedures such as dusting, drenching, impregnation, spraying, or the like. They can be formulated by conventional procedures to provide antimicrobial compositions by admixture of one or more acetamidine compounds of the invention with an adjuvant such as surface active dispersing agents, inert liquid carriers, finely divided solid carriers, and the like.

In representative operations, complete inhibition and control of *Staphylococcus aureus*, *Bacillus subtilis*, *Trichophyton mentagrophytes*, *Candida pelliculosa*, *Pullularia pullulans*, *Ceratocystis ips* and *Cephaloascus fragrans* is obtained when nutrient agar containing either 500 parts of 2-(4-tert-butylphenylthio)acetamidine hydrochloride or 2-(4-tert-butylphenylthio)acetamidoxime hydrochloride per million parts of ultimate composition are inoculated with said organisms and incubated under conditions conducive to microbial growth.

In other representative operations, 2-(4-chlorophenylthio)acetamidine hydrochloride, 2-(4-chlorophenylthio)acetamidoxime hydrochloride, and 2-(4-tert-butylphenylthio)acetamidine hydrochloride are found effective in inhibiting the adenosine diphosphate (ADP)-induced aggregation of sheep platelets in a method similar to that of Zucker et al., Thromb, Diath. Haemorrh. 18, 713 (1967). Said compounds are also found to protect mice from thrombitic response induced by intravenous administration of 0.25 millimoles per kilogram of ADP, when the compounds are administered intragastrically one hour before administration of the ADP challenge. The above-named compounds are found to have ED-50's (dosage protecting 50 percent of the mice from ADP challenge) of 40, 71, 160, 57, and 47 milligrams, respectively, of test compound per kilogram of animal body weight.

In other operations 2-(4-chlorophenylthio)acetamidine hydrochloride and 2-(4-chlorophenylthio)acetamidoxime hydrochloride are administered orally to separate groups of mice at a dosage rate of 60 milligrams of test compound per kilogram of animal body weight. Urine is collected in sterile vessels during the 24 hour period following administration of the test compound, and sterile paper discs are saturated in the urine and allowed to dry. The discs are then placed on the surface of nutrient agar media seeded with one of E. coli, Ps. aeruginosa and Proteus species and the plates are incubated under conditions conductive to microbial growth zones of inhibition of microbial growth 12, 8 and 8 millimeters in radial length are observed for E. coli, Ps. aeruginosa and Proteus vulgaris with test compound 2-(4-chlorophenylthio)acetamidine hydrochloride, and zones 20, 24 and 19 millimeters in radial length are observed with the corresponding oxime test compound. In identical operations, no inhibition of any of the test organisms is observed with 2-(4-chlorophenoxy)acetamidine hydrochloride of cummings et al. Chemical Abstracts 44, 8397, (1950) or its corresponding oxime; with the 2-(4-methylphenylthio)acetamidine hydrochloride of Craver et al., J. Pharmacol. Exptl. Therap. 99, 353 (1950), or the corresponding oxime.

The substituted phenylthioacetonitrile starting materials can be prepared by the reaction of the corresponding thiophenol with chloroacetonitrile in alcoholic sodium hydroxide. In a representative procedure, a solution of 100 grams of 4-tert-butylthiophenol and 45.3 grams chloroacetonitrile in 225 milliliters of 95 percent ethanol is stirred at room temperature while a solution of 24 grams sodium hydroxide in 36 milliliters water is added dropwise until the mixture remains alkaline to phenolphthalein. Slight spontaneous warming occurs during the addition. The mixture is then diluted with an equal volume of water and extracted twice with ether. The ether extract is washed with water, dried over sodium sulfate, and distilled, yielding the 2-(4-tert-butylphenylthio)acetonitrile as a liquid boiling at 153°–6° C. under a pressure of 4 millimeters of mercury.

I claim:
1. A substituted phenylthio amidine compound selected from the group consisting of compounds corresponding to the formula:

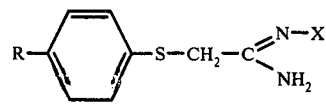

wherein R represents tertiary butyl and X represents hydrogen, and the salts thereof of pharmaceutically-acceptable acids.

2. A compound of claim 1 wherein the compound is 2-(4-tert-butylphenylthio)acetamidine hydrochloride.

* * * * *